United States Patent
Sekiguchi et al.

(10) Patent No.: US 11,771,122 B2
(45) Date of Patent: Oct. 3, 2023

(54) FOAM BODY AND METHOD FOR MANUFACTURING THE SAME

(71) Applicant: NITTO DENKO CORPORATION, Ibaraki (JP)

(72) Inventors: Yuka Sekiguchi, Ibaraki (JP); Takahisa Konishi, Ibaraki (JP); Tomoaki Hishiki, Ibaraki (JP); Tomoko Sudo, Ibaraki (JP); Shinya Hashiguchi, Ibaraki (JP); Yusuke Kamano, Ibaraki (JP)

(73) Assignee: NITTO DENKO CORPORATION, Ibaraki (JP)

( * ) Notice: Subject to any disclaimer, the term of this patent is extended or adjusted under 35 U.S.C. 154(b) by 0 days.

(21) Appl. No.: 17/762,362

(22) PCT Filed: Sep. 10, 2021

(86) PCT No.: PCT/JP2021/033401
§ 371 (c)(1),
(2) Date: Mar. 21, 2022

(87) PCT Pub. No.: WO2022/070845
PCT Pub. Date: Apr. 7, 2022

(65) Prior Publication Data
US 2022/0408774 A1 Dec. 29, 2022

(30) Foreign Application Priority Data
Sep. 29, 2020 (JP) .................................. 2020-163927

(51) Int. Cl.
*C08J 9/28* (2006.01)
*A23L 29/256* (2016.01)
(Continued)

(52) U.S. Cl.
CPC ........... *A23L 29/256* (2016.08); *A23L 29/015* (2016.08); *A23L 29/262* (2016.08)

(58) Field of Classification Search
CPC ..... A23L 29/256; A23L 29/262; A23L 29/015
(Continued)

(56) References Cited

U.S. PATENT DOCUMENTS

2007/0065555 A1 3/2007 Soane et al.
2018/0215892 A1 8/2018 Girod Fullana et al.

FOREIGN PATENT DOCUMENTS

CN 110915940 A 3/2020
JP 2644626 B2 8/1997
(Continued)

OTHER PUBLICATIONS

Office Action dated Feb. 22, 2022 for corresponding Japanese Patent Application No. 2021-576522, along with an English machine translation.

(Continued)

*Primary Examiner* — Brent T O'Hern
(74) *Attorney, Agent, or Firm* — HAUPTMAN HAM, LLP

(57) ABSTRACT

The present invention provides a foam body suitable for producing a cultured meat having a good texture. The foam body of the present invention includes alginic acid and/or an alginate. The foam body has an elastic modulus M, as determined by a test, of $8\times10^4$ Pa or less. In the test, the foam body is immersed in $22\pm3°$ C. water for 4 hours to prepare a specimen having a post-immersion thickness of $5\pm1$ mm. Stress and strain caused in the specimen are measured by applying a load to the specimen for 5 seconds to compress the specimen in a thickness direction at 0.5 mm/sec. A stress caused in the specimen when the specimen is compressed by 10% of an initial thickness is determined, and a value
(Continued)

obtained by dividing the stress by a corresponding strain is determined as the elastic modulus M.

11 Claims, 8 Drawing Sheets

(51) Int. Cl.
*A23L 29/262* (2016.01)
*A23L 29/00* (2016.01)

(58) Field of Classification Search
USPC .......................................................... 426/564
See application file for complete search history.

(56) References Cited

FOREIGN PATENT DOCUMENTS

| | | | |
|---|---|---|---|
| JP | 2007-505183 A | 3/2007 | |
| JP | 2009-529926 A | 8/2009 | |
| JP | 2020-523015 A | 8/2020 | |
| WO | 94/00512 A1 | 1/1994 | |
| WO | 2005/023323 A1 | 3/2005 | |
| WO | WO-2007008560 A2 * | 1/2007 | ............ A23C 11/10 |
| WO | 2007/103209 A2 | 9/2007 | |
| WO | 2018/227016 A1 | 12/2018 | |

OTHER PUBLICATIONS

Decision to Grant dated Apr. 26, 2022 for corresponding Japanese Patent Application No. 2021-576522, along with an English machine translation.

International Search Report dated Nov. 22, 2021, for corresponding International Patent Application No. PCT/JP2021/033401, along with an English Translation.

Written Opinion dated Nov. 22, 2021, for corresponding International Patent Application No. PCT/JP2021/033401.

* cited by examiner

FOAM BODY AND METHOD FOR MANUFACTURING THE SAME

CROSS-REFERENCE TO RELATED APPLICATION

This application is a National Stage of International Application No. PCT/JP2021/033401, filed on Sep. 10, 2021, which designates the United States and was published in Japan, and which is based upon and claims priority to Japanese Patent Application No. 2020-163927 filed on Sep. 29, 2020 in the Japan Patent Office. All of the aforementioned applications are hereby incorporated by reference in their entireties.

TECHNICAL FIELD

The present invention relates to a foam body suitable for a scaffold for cultured meat and a method for manufacturing the foam body.

BACKGROUND ART

Recently, demand for meat is expected to increase with an increasing world population. To meet the increasing demand for meat in the future, increasing production of conventional protein sources by enhancing production efficiency is insufficient, and new protein sources need to be developed. New protein sources are, for example, plant-based meat produced from plants, meat produced from insects, and cultured meat produced by culturing microorganisms or cells themselves. "Plant-based meat" is a processed food including a plant protein, such as soy beans, as a raw material and produced by adding an additive to a plant protein and shaping the mixture. Plant-based meat is also called "fake meat". "Cultured meat" means a meat produced by culturing muscle cells using regenerative medicine techniques, and it is also called "clean meat".

One of the advantages of cultured meat is its safety. For example, in the course of production and processing of meat, there is always a risk of introducing a pathogen that can cause food poisoning. On the other hand, since cultured meat is cultured under nearly-axenic conditions, introduction of a pathogen is less likely to happen. Furthermore, there is a study which says that production of cultured meat not only can reduce processing cost, but also can reduce the amount of greenhouse gas emissions by 96% compared to production of meat by a conventional production process. Cultured meat has therefore been attracting attention also from an environment perspective. Cultured meats reported so far are in minced form.

CITATION LIST

Patent Literature

Patent Literature 1: JP 2644626 B2
Patent Literature 2: JP 2009-529926 A
Patent Literature 3: JP 2007-505183 A

SUMMARY OF INVENTION

Technical Problem

To produce a chunk of meat of a certain size, such as steak, sashimi, a fillet, etc., it is necessary to culture muscle cells three-dimensionally using a scaffold. The scaffold is preferably a porous body made of an edible material such as a polysaccharide. Patent Literatures 1 to 3 disclose examples of a porous body including a polysaccharide. Specifically, Patent Literatures 1 to 3 disclose foam bodies including alginic acid which is a polysaccharide.

However, according to a study by the present inventors, it is difficult to produce a cultured meat having a good texture using conventional foam bodies.

Therefore, the present invention aims to provide a foam body suitable for producing a cultured meat having a good texture.

Solution to Problem

As a result of a detailed study, the present inventors have found that the texture of cultured meat changes depending on physical properties of a scaffold. The present inventors have further conducted a study on the basis of the finding and completed the present invention.

The present invention provides a foam body including alginic acid and/or an alginate, wherein the foam body has an elastic modulus M, as determined by a test, of $8 \times 10^4$ Pa or less, in the test, the foam body is immersed in 22±3° C. water for 4 hours to prepare a specimen having a post-immersion thickness of 5±1 mm, stress and strain caused in the specimen are measured by applying a load to the specimen for 5 seconds to compress the specimen in a thickness direction at 0.5 mm/sec, a stress caused in the specimen when the specimen is compressed by 10% of an initial thickness is determined, and a value obtained by dividing the stress by a corresponding strain is determined as the elastic modulus M.

The present invention also provides a foam body manufacturing method including:

a step (i) of foaming a solution containing a foaming agent; and a step (ii) of adding an alginate to the foamed solution, wherein the foaming agent includes two or more additional polysaccharides other than alginic acid and an alginate.

The present invention also provides a foam body including: alginic acid and/or an alginate; glucomannan; and a cellulose derivative.

Advantageous Effects of Invention

The present invention can provide a foam body suitable for producing a cultured meat having a good texture.

DESCRIPTION OF EMBODIMENTS

Figure 1A:
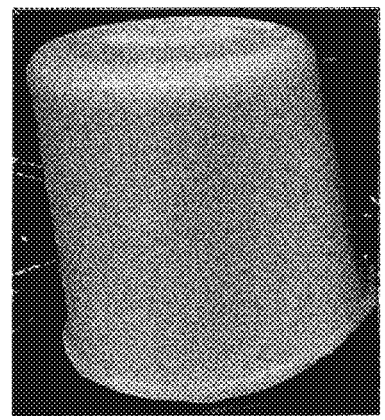
FIG. 1A shows a gel product taken out of a cup in Example 1.

Hereinafter, the present invention will be described in detail. The following description is not intended to limit the present invention to specific embodiments.

A foam body of the present embodiment includes alginic acid and/or an alginate. The foam body is, for example, edible. Saying that "the foam body is edible" herein means that the foam body consists of a substance approved as food or a food additive, for example, by a law in a country.

In the present embodiment, the foam body has an elastic modulus M, as determined by a test, of $8\times10^4$ Pa or less. In the test for measuring the elastic modulus M, first, the foam body to be evaluated is prepared. This foam body is preferably in a dry state. The term "dry state" of a foam body herein means that the water content in the foam body is 1 wt % or less. The foam body to be evaluated may be a foam body with which cultured meat has not been produced or may be a foam body obtained by causing a reaction of cultured meat with, for example, a proteolytic enzyme to remove muscle cells from the cultured meat. In the case of drying the foam body to be evaluated, the drying conditions are not particularly limited. The drying temperature is, for example, 60° C. or higher, and the drying time is, for example, 1 hour or more. Next, the foam body is cut to a thickness of 5±1 mm. A specific shape of the cut-out foam body is, for example, a cube having a length of 10 mm, a width of 10 mm, and a thickness of 5±1 mm. When the foam body to be evaluated has a thickness of less than 4 mm, the measurement test may be performed using a laminate of a plurality of the foam bodies.

Next, the foam body is immersed in 22±3° C. water for 4 hours to prepare a specimen having a post-immersion thickness of 5±1 mm. When the foam body is immersed in the water, the entire foam body is preferably in contact with the water. After the immersion of the foam body in the water, excess water on the surfaces of the foam body is preferably removed. Incidentally, the foam body may expand by the immersion in water and the thickness thereof may change slightly. When the post-immersion thickness of the foam body is greater than 6 mm, the foam body is, for example, cut to a thickness of 5±1 mm and the resulting foam body is used as a specimen. Next, the specimen is set on a commercially-available dynamic viscoelastic measurement apparatus (for example, RSA-G2 manufactured by TA Instruments) for solids. Stress and strain caused in the specimen are measured using the measurement apparatus by applying a load to the specimen for 5 seconds to compress the specimen in a thickness direction at 0.5 mm/sec. Then, a stress caused in the specimen when the specimen is decompressed by 10% of an initial thickness (when a compression rate is 10%) is determined. A value obtained by dividing the determined stress by a corresponding strain (a strain in the specimen at a compression rate of 10%) is determined as the elastic modulus M of the foam body.

The elastic modulus M of the foam body is not particularly limited as long as the elastic modulus M of the foam body is $8\times10^4$ Pa or less. The elastic modulus M of the foam body is preferably $6\times10^4$ Pa or less, more preferably $5\times10^4$ Pa or less, even more preferably $4\times10^4$ Pa or less, and particularly preferably $3\times10^4$ Pa or less, and may be $2\times10^4$ Pa or less. The lower limit of the elastic modulus M of the foam body is not particularly limited. The elastic modulus M of the foam body is, for example, $1\times10^3$ Pa or more, preferably $2\times10^3$ Pa or more, more preferably $3\times10^3$ Pa or more, and even more preferably $4\times10^3$ Pa or more, and may be $8\times10^3$ Pa or more, in some cases, or $1\times10^4$ Pa or more.

According to a study by the present inventors, the elastic modulus M, determined by the above test, of the foam body can be used as a measure of the texture of cultured meat. The foam body having an elastic modulus M of $8\times10^4$ Pa or less has a texture similar to that of meat (particularly raw meat) and is suitable for production of cultured meat having a good texture.

(Components in Foam Body)

As described above, the foam body includes the alginic acid and/or the alginate. The alginic acid is a polysaccharide included, for example, in seaweeds, and has a structural unit (M-block) derived from β-D-mannuronic acid and a structural unit (G-block) derived from α-L-guluronic acid. In the alginic acid, the structural units are bonded via a 1,4-glycosidic bond. The G-block content in the alginic acid is, for example, but not particularly limited to, 30 mol % or more, preferably 40 mol % or more, and more preferably 50 mol % or more. The upper limit of the G-block content may be 90 mol % or 80 mol %. The G-block content may be 31 mol % to 63 mol %.

The alginate included in the foam body is, for example, a salt of alginic acid and a divalent metal ion. For example, in the alginate, at least one G-block included in the alginic acid forms an ionic bond with the divalent metal ion. In other words, in the alginate included in the foam body, the alginic acid partially forms a salt with the divalent metal ion. The alginate has, for example, a crosslinking structure mediated by the divalent metal ion. Examples of the divalent metal ion include a calcium ion, a barium ion, an iron ion, a zinc ion, a copper ion, and an aluminum ion, and the divalent metal ion is preferably a calcium ion.

A sum of the alginic acid content and the alginate content in the foam body is, for example, but not particularly limited to, 10 wt % or more, preferably 20 wt % or more, more preferably 30 wt % or more, and even more preferably 40 wt % or more. The upper limit of the sum is not particularly limited, and is, for example, 80 wt %, preferably 70 wt %, and more preferably 60 wt %. The sum may be 22 wt % to 58 wt %. Herein, the "content in the foam body" refers to the content in the foam body in the dry state, unless otherwise specified.

The foam body may further include an additional polysaccharide (P) other than alginic acid and an alginate, and preferably includes two or more additional polysaccharides (P). The two or more additional polysaccharides (P) may associate with each other in the foam body. The additional polysaccharide (P), for example, functions as a foaming agent in manufacturing the foam body. As the additional polysaccharide (P), the foam body includes, for example, at least one selected from the group consisting of glucomannan (konjac-mannan) and a cellulose derivative and preferably includes both glucomannan and a cellulose derivative.

Glucomannan is a polysaccharide included, for example, in konjac corm, and has a structural unit (glucose unit) derived from glucose and a structural unit (mannose unit) derived from mannose. In the glucomannan, the structural units are bonded via a 1,4-glycosidic bond. In the glucomannan, a molar ratio of the mannose unit to the glucose unit is not particularly limited, and is, for example, 0.5 to 2 and may be 0.5 to 1.6.

The cellulose derivative has a structure in which a substituent is introduced in cellulose. This substituent is preferably the one that functions as a hydrophobic group in the cellulose derivative. The cellulose derivative is, for example, a cellulose ether. Examples of the cellulose ether include alkyl celluloses such as methylcellulose (MC), hydroxyalkyl celluloses such as hydroxypropyl celluloses (HPC) and hydroxyethyl cellulose (HEC), hydroxyalkylalkylcelluloses such as hydroxypropyl methylcellulose (HPMC), and carboxyalkyl celluloses such as carboxymethyl cellulose (CMC). The cellulose derivative preferably includes hydroxypropyl methylcellulose.

The additional polysaccharide (P) content in the foam body is not particularly limited, and is, for example, 0.5 wt % or more, preferably 5 wt % or more, more preferably 10 wt % or more, and even more preferably 20 wt % or more. The upper limit of the additional polysaccharide (P) content is not particularly limited, and is, for example, 90 wt %, preferably 80 wt %, and more preferably 70 wt %. The additional polysaccharide (P) content may be 31 wt % to 54 wt %.

When the foam body includes the glucomannan, the glucomannan content in the foam body is not particularly limited, and is, for example, 0.5 wt % to 5.0 wt %, and may be 1.9 to 3.2 wt %. When the foam body includes the cellulose derivative, the cellulose derivative content in the foam body is not particularly limited, and is, for example, 20 wt % to 80 wt % and may be 34 to 52 wt %. A weight ratio between the glucomannan and the cellulose derivative in the foam body is not particularly limited, and is preferably 0.1:99.9 to 9.9:90.1.

In another aspect, the present invention provides a foam body including: the alginic acid and/or the alginate; the glucomannan; and the cellulose derivative.

The foam body may further include a compound (C) that generates a divalent metal ion. The compound (C) can generate the divalent metal ion, for example, by contact with an acid. Examples of the divalent metal ion include those described above for the alginate. The compound (C) is, for example, a salt including the divalent metal ion. Examples of the salt include carbonates such as calcium carbonate. The compound (C), especially calcium carbonate, is a component suitable for adjusting hardness of the foam body. The compound (C) may be present as a salt residue in the foam body, or may be consumed by a later-described crosslinking reaction of alginic acid molecules. The compound (C) may remain in a solid state in the foam body.

The content of the compound (C), especially calcium carbonate, in the foam body is not particularly limited, and is, for example, 20 wt % or less, preferably 18 wt % or less, and more preferably 15 wt % or less, and may be 12 wt % or less. The lower limit of the compound (C) content is, for example, but not particularly limited to, 0.1 wt %. The compound (C) content may be 3.5 wt % to 15 wt %, 3.8 wt % to 15 wt %, or, in some cases, 3.5 wt % to 12 wt %. The hardness of the foam body tends to be appropriately adjusted by adjusting the compound (C) content in the above range. However, the foam body may be free of the compound (C).

As described later, in a foam body manufacturing method according to the present embodiment, for example, while a solution (S) containing a foaming agent is being stirred, the alginate is added to the solution (S) and then the compound (C) and an acid generator are added thereto. If a large amount of the compound (C) is added to the solution (S) to adjust the compound (C) content in the foam body at a high level, gelation of the solution (S) tends to progress rapidly. In that case, the flowability of the solution (S) rapidly decreases and the solution (S) is rapidly solidified. The compound (C) content in the foam body is preferably adjusted to 20 wt % or less from the view point of easy manufacturing of the foam body.

The foam body may further include an acid generator and/or a decomposition of an acid generator. The acid generator is an undecomposed residue in the foam body. Examples of the acid generator include compounds that forms an acid group, such as a carboxyl group, by hydrolysis. A specific example of the acid generator is glucono-delta-lactone. A specific example of the decomposition of an acid generator is gluconic acid. The sum of the content of the acid generator and the content of the decomposition of an acid generator in the foam body is, for example, 50 wt % or less and preferably 30 wt % or less. The sum may be 6.8 wt % to 27 wt %. The foam body may be free of the acid generator or may be free of the decomposition of an acid generator.

The foam body may include an additional component other than the polysaccharide, the compound (C), the acid generator, and the decomposition of an acid generator, but is preferably substantially free of such an additional component. Examples of the additional component include a plasticizer (softener) and a surfactant including a low-molecular compound. The additional component content in the foam body is, for example, 10 wt % or less, preferably 5 wt % or less, and more preferably 1 wt % or less.

(Foam Body Manufacturing Method)

A foam body manufacturing method according to the present embodiment includes:

a step (i) of foaming a solution (S) containing a foaming agent; and a step (ii) of adding an alginate to the foamed solution (S).

In the step (i), the foaming agent includes, for example, two or more additional polysaccharides (P) other than alginic acid and an alginate. As the additional polysaccharide (P) can be used those described above as the additional polysaccharide (P). The foaming agent preferably includes both the glucomannan and the cellulose derivative (especially hydroxypropyl methylcellulose). When the foaming agent includes the glucomannan and the cellulose derivative, the mannose unit of the glucomannan tends to interact with the substituent, especially a hydrophobic group, included in the cellulose derivative in the solution (S). This interaction causes association of the glucomannan and the cellulose derivative. It is likely that the association of the glucomannan and the cellulose derivative not only leads to easy foaming of the solution (S) in the step (i) but also improves the elasticity of the foam formed in the step (i). Moreover, the shape of the foam is likely to be maintained for a longer time.

The concentration of the foaming agent in the solution (S) is, for example, but not particularly limited to, 0.05 wt % to 5 wt %. In one example, the concentration of the glucomannan in the solution (S) is, for example, 0.05 wt % to 0.5 wt % and preferably 0.1 wt % to 0.3 wt %. The concentration of the cellulose derivative in the solution (S) is, for example, 0.5 wt % to 5 wt % and preferably 1 wt % to 3 wt %.

The solution (S) contains, for example, a solvent in addition to the foaming agent. The solvent is typically water.

In the step (i), the method for foaming the solution (S) is not particularly limited, and a known method can be used. For example, the solution (S) may be foamed by stirring the solution (S) using a commercially-available homogenizer. The rate, duration, etc. of stirring of the solution (S) can be determined as appropriate according to the viscosity and composition of the solution (S). The step (i) is, for example, performed at room temperature (22±3° C.). In the step (i), it is preferred that the solution (S) be foamed wholly.

In the step (ii), examples of the alginate added to the solution (S) include a salt of alginic acid and an alkali metal ion such as a sodium ion or a potassium ion. The alginate is preferably sodium alginate. The alginate added to the solution (S) is typically substantially free of a divalent metal ion.

In the step (ii), the alginate is preferably added to the solution (S) while the solution (S) is being stirred. In the step (ii), the viscosity of the solution (S) increases upon the addition of the alginate to the solution (S). Consequently, the shape of the foam formed from the solution (S) is easily maintained.

In the step (ii), the alginate is added to the solution (S) so that the concentration of the alginate in the solution (S) will be, for example, 1 wt % to 3 wt % and preferably 1 wt % to 2 wt %.

The manufacturing method of the present embodiment further includes, for example, a step (iii) of adding a compound (C) that generates a divalent metal ion and an acid generator to the solution (S) after the step (ii) to produce a gel product. As the compound (C) and the acid generator can be used those described above.

It is preferred that in the step (iii), first, the compound (C) be added to the solution (S) and then the acid generator be slowly added thereto. In the step (iii), the compound (C) and the acid generator are added, for example, while the solution (S) is being stirred.

In the step (iii), the addition of the acid generator to the solution (S) causes generation of an acid from the acid generator. Specifically, the acid generator is hydrolyzed in the solution (S) to form an acid group. As the acid group is formed, the hydrolyzed acid generator functions as an acid. The acid reacts with the compound (C), whereby the divalent metal ion is generated from the compound (C).

The divalent metal ion generated from the compound (C) forms an ionic bond with the G-block of the alginate. Specifically, the metal ion (alkali metal ion) included in the alginate is exchanged with the divalent metal ion. A plurality of alginic acid molecules are thereby cross-linked via the divalent metal ion. This crosslinking reaction triggers gelation of the solution (S). The solution (S) turns into the gel product by the gelation.

A crosslinking reaction of a plurality of alginic acid molecules via the divalent metal ion is commonly an irreversible reaction. That is, the gel product obtained in the step (iii) of the present embodiment is unlikely to return to the solution (S). Consequently, a foam body produced from the gel product tends to have high heat resistance. A cultured meat produced using the highly heat-resistant foam body as a scaffold is likely to maintain its shape throughout and after cooking. Thus, the foam body having high heat resistance is particularly suitable for a scaffold for cultured meat to be cooked.

In the case where a polysaccharide (for example, chitosan) that is different from an alginate is used in the step (ii) instead of the alginate, the gelation of the solution (S) can also progress in the step (iii). However, when the different polysaccharide is used, it is necessary to heat and then cool the solution (S) to accelerate the gelation of the solution (S). On the other hand, the gelation of the solution (S) by the crosslinking reaction of the plurality of alginic acid molecules is advantageous in that the gelation of the solution (S) progresses relatively fast even without heating the solution (S). Moreover, as described above, the foam body produced using the gel product obtained by the crosslinking reaction of the plurality of alginic acid molecules is advantageous in that the foam body has higher heat resistance than a foam body produced using the different polysaccharide.

In the step (iii), the solution (S) may be cooled during and/or after the addition of the acid generator in order to appropriately control a rate of the gelation of the solution (S). In the step (iii), the gelation tends to progress uniformly by appropriate control of the gelation rate. It should be noted that non-uniform progress of the gelation tends to increase the elastic modulus M and apparent density of the foam body formed from the resulting gel product. The gelation rate can be evaluated on the basis of a duration (duration before the start of the gelation) from the addition of the acid generator to loss of the flowability of the solution (S). In one example, the duration before the start of the gelation is preferably 5 seconds or more and more preferably 10 seconds or more. The term "loss of the flowability of the solution (S)" refers to the state in which a change in the shape of the solution (S) cannot be visually confirmed when a container of the solution (S) is tilted at 45°.

In the step (iii), the compound (C) is added to the solution (S) so that the concentration of the compound (C) in the solution (S) will be, for example, 0.1 wt % to 1.0 wt % or, in some cases, 0.2 wt % to 1.0 wt %. Furthermore, the acid generator is added to the solution (S) so that the concentration of the acid generator in the solution (S) will be, for example, 0.1 wt % to 1.8 wt % or, in some cases, 0.3 wt % to 1.3 wt %.

In the manufacturing method of the present embodiment, the rate of the gelation of the solution (S) tends to be affected by a weight ratio R1 of an amount of the compound (C) added in the step (iii) to an amount of the alginate added in the step (ii) and a weight ratio R2 of an amount of the acid generator added in the step (iii) to an amount of the compound (C) added in the step (iii). According to a study by the present inventors, the elastic modulus M of the resulting foam body tends to be affected too by the weight ratios R1 and R2. Furthermore, the pH of a culture liquid which is for culturing muscle cells and in which the foam body is immersed tends to be affected too by the weight ratios R1 and R2.

The weight ratio R1 is, for example, 0.05 or more, preferably 0.08 or more, more preferably 0.1 or more, and even more preferably 0.2 or more. The weight ratio R1 is, for example, 1.0 or less, preferably 0.8 or less, more preferably 0.7 or less, and even more preferably 0.6 or less. The weight ratio R1 is preferably 0.05 to 1.0, more preferably 0.08 to 0.8, even more preferably 0.1 to 0.7, and particularly preferably 0.2 to 0.6.

The weight ratio R2 is, for example, 0.5 or more, preferably 0.7 or more, and more preferably 0.9 or more. The weight ratio R2 is, for example, 4.0 or less, preferably 3.8 or less, more preferably 3.6 or less, and even more preferably 3.4 or less. The weight ratio R2 is preferably 0.5 to 4.0 and more preferably 0.9 to 3.6.

The manufacturing method of the present embodiment further includes, for example, a step (iv) of drying the gel product obtained in the step (iii) to produce a dried product. In the step (iv), for example, the solvent (water) derived from the solution (S) is removed from the gel product. The solvent content in the dried product obtained in the step (iv) is, for example, 1 wt % or less. In the step (iv), the conditions for drying the gel product are not particularly limited. The temperature at which the gel product is dried is, for example, 60° C. or higher. The time during which the gel product is dried is, for example, 1 hour or more.

The manufacturing method of the present embodiment may further include a cutting step of, before the step (iv), cutting the gel product into a given shape and/or, after the step (iv), cutting the dried product into a given shape. The cutting step is preferably performed for the gel product in terms of ease of cutting. The foam body having a shape suitable for production of cultured meat can be produced by the cutting step. Examples of the given shape include a sheet shape and a cubic shape.

A surface of the dried product produced by the steps (i) to (iv) of the manufacturing method of the present embodiment tends to have a dense layer called "skin layer". A culture liquid for culturing muscle cells is less likely to permeate into the dried product having the skin layer. Therefore, in the above cutting step, the dried product is preferably cut such that the skin layer is removed. The manufacturing method of the present embodiment may not include the cutting step. In the manufacturing method of the present embodiment, the dried product obtained in the step (iv) may be considered a foam body.

(Structure and Physical Properties of Foam Body)

Next, the structure and physical properties of the foam body of the present embodiment will be described. The structure and physical properties of the foam body hereinafter refer to those of the foam body in the dry state, unless otherwise specified.

The shape of the foam body of the present embodiment is not particularly limited, and can be adjusted as appropriate according to the shape of a cultured meat to be produced. In one example, the foam body may be in the shape of a sheet or cube having a thickness of 1 to 30 mm.

The foam body of the present embodiment includes, for example, a plurality of pores. The plurality of pores are arranged, for example, three-dimensionally and continuously. That is, the foam body has, for example, a plurality of continuous pores. However, the foam body may further have an isolated pore in addition to the continuous pores. In the case where the skin layer has been removed by the above cutting step, the pores are not blocked by the skin layer. In other words, the foam body in the dry state has, for example, a pore opening at a surface.

An average pore diameter of the pores included in the foam body is, for example, but not particularly limited to, 50 µm to 500 µm. The average pore diameter of the foam body can be determined by the following method. First, a cross-section of the foam body is observed using a scanning electron microscope. The area of a particular pore on the resulting electron microscope image is calculated by image processing. The diameter of a circle having the same area as the calculated area is regarded as the pore diameter of the particular pore (the diameter of the pore). The diameter is calculated for any number (at least 50) of the pores, and the average of the calculated values is regarded as the average pore diameter of the foam body.

A porosity of the foam body is, for example, but not particularly limited to, 80% or more, preferably 90% or more, and more preferably 95% or more. The upper limit of the porosity of the foam body is, for example, but not particularly limited to, 99%. The porosity of the foam body can be measured in the following manner. First, the volume and weight of the foam body to be evaluated are determined. The porosity of the foam body can be calculated by substituting the volume and weight into the following expression (1). In the expression (1), V represents the volume ($cm^3$), W represents the weight (g), and D represents the true density ($g/cm^3$) of the foam body. The true density can be calculated, for example, from the volume and weight of a solid obtained by performing the steps (i) to (iv) without foaming the solution (S) in the above manufacturing method. The true density can also be calculated on the basis of the specific gravities of the components included in the foam body.

$$\text{Porosity } (\%) = 100 \times [V - (W/D)]/V \qquad (1)$$

An apparent density of the foam body is, for example, but not particularly limited to, 0.1 $g/cm^3$ or less, preferably 0.07 $g/cm^3$ or less, more preferably 0.05 $g/cm^3$ or less, and even more preferably 0.04 $g/cm^3$ or less. The lower limit of the apparent density of the foam body is, for example, but not particularly limited to, 0.02 $g/cm^3$. The apparent density of the foam body can be calculated from the volume and weight of the foam body to be evaluated. The smaller the apparent density of the foam body is, the more likely the distance between two neighboring pores in the foam body is to be small, i.e., a pore wall is to be thin. The foam body having a thin pore wall tends to have a low elastic modulus M due to its low compressive strength.

A density of the foam body in a wet state is, for example, but not particularly limited to, 0.3 $g/cm^3$ to 1.6 $g/cm^3$. In the foam body in a wet state, a ratio of the weight of water to the weight of the foam body itself (the foam body in the dry state) is, for example, 500 wt % or more. The foam body in a wet state can be obtained, for example, by immersing the foam body in the dry state in 22±3° C. water for 4 hours. The density of the foam body in a wet state can be calculated from the volume and wight of the foam body to be evaluated.

A foaming ratio of the foam body is, for example, but not particularly limited to, 25 or more, preferably 30 or more, and more preferably 40 or more. The upper limit of the foaming ratio of the foam body is, for example, but not particularly limited to, 100. The foaming ratio of the foam body means a ratio of the true density of the foam body to the apparent density of the foam body in the dry state.

The foam body desirably does not affect conditions for culturing muscle cells. For example, when the foam body is immersed in a culture liquid for muscle cells, the foam body preferably does not greatly decrease the pH of the culture liquid. In one example, when the following pH test 1 is performed for the foam body, the pH of the water used is preferably more than 6 and more preferably 7 to 10.

pH test 1: First, the foam body in the dry state having a length of 10 mm, a width of 6 mm, and a thickness of 1 mm is prepared as a specimen. The specimen is immersed in 1.5 mL of 22±3° C. water (distilled water) for 18 hours. The pH of the water in which the specimen has been immersed is measured using a commercially-available pH meter.

Additionally, when the following pH test 2 is performed for the foam body, the pH of water used is preferably more than 6 and more preferably 7 to 10.

pH test 2: First, the foam body in the dry state having a length of 10 mm, a width of 6 mm, and a thickness of 1 mm is prepared as a specimen. The specimen is immersed in 50 mL of 22±3° C. water (distilled water) for 18 hours. The specimen is taken out of the water, and water on its surfaces is removed. The specimen is immersed in 1.5 mL of 22±3° C. water separately prepared. The pH of the water in which the specimen is immersed is measured using a commercially-available pH meter.

In the case where the foam body is immersed in a culture liquid, the culture liquid is preferably neutral (around pH 7). However, even when the pH of the culture liquid is increased to some degree by immersing the foam body in the culture liquid, the pH of the culture liquid can be adjusted appropriately by adjusting conditions for culturing muscle cells, particularly the amount of $CO_2$ gas introduced.

The structure of the foam body preferably allows a culture liquid for muscle cells to easily permeate in the foam body. For example, a culture liquid easily permeates in the foam body having no skin layer and having pores opening at the surface. In one example, when the following permeation test is performed for the foam body, the maximum diameter of a mark of an aqueous solution formed on a surface of the foam body is preferably 10 mm or more and more preferably 15 mm or more.

Permeation test: First, the foam body in the dry state having a length of 30 mm, a width of 30 mm, and a thickness of 2 mm is prepared as a specimen. A drop of 15 μL of an aqueous solution containing a food dye at a concentration of 0.67 wt % is dropped onto a principal surface (a surface having the largest area) of the specimen at room temperature (22±3° C.). Ten seconds later, a mark of the aqueous solution (a mark of the food dye permeated in the foam body) formed on the surface of the specimen is measured for its maximum diameter.

Patent Literature 1 discloses a polysaccharide foam body produced using alginic acid. However, in Patent Literature 1, an inedible compound such as sodium dodecyl sulfate is used as a foaming agent.

Patent Literatures 2 and 3 disclose foam bodies produced using alginic acid. However, as can be seen from the results of Comparative Examples later described, it is difficult to produce a foam body having an elastic modulus M of $8\times10^4$ Pa or less under the manufacturing conditions disclosed in Patent Literatures 2 and 3. For example, in Patent Literatures 2 and 3, the foam bodies are produced in the presence of a plasticizer (softener) in order to use the foam bodies as a wound dressing material and a treatment material used in the oral cavity. A plasticizer tends to decrease the foamability of a solution containing a foaming agent. As can be understood from the result of Comparative Example 1 later described, insufficient foamability of the solution makes it difficult to adjust the elastic modulus M of the resulting foam body to $8\times10^4$ Pa or less. Moreover, as is obvious from the results of Comparative Examples 2 to 4 later described, even when a foam body is produced in the absence of a plasticizer, it is difficult to adjust the elastic modulus M of the foam body to $8\times10^4$ Pa or less under the conditions disclosed in Patent Literatures 2 and 3.

In Patent Literatures 2 and 3, the foam bodies are produced using a relatively large amount of an acid generator. When the amount of the acid generator is excessive relative to that of the compound (C) in manufacturing of a foam body, gelation of the solution (S) is likely to non-uniformly progress because of a high-rate gelation of the solution (S). The elastic modulus M of a foam body is expected to be increased further by simply increasing, under the manufacturing conditions in Patent Literatures 2 and 3, the amount of the compound (C) added relative to the amount of the acid generator added.

There is a soluble polysaccharide gel in pores of the foam body of Patent Literature 2. A space where muscle cells can grow is limited in such a foam body, and it is expected to be difficult to culture muscle cells adequately therewith.

As described above, the foam body of the present embodiment has an elastic modulus M of $8\times10^4$ Pa or less and thus has a texture similar to that of meat (particularly raw meat). The foam body is therefore suitable for producing a cultured meat having a good texture. In another aspect, the present invention provides a cultured meat including a foam body including alginic acid and/or an alginate, the foam body having an elastic modulus M of $8\times10^4$ Pa or less. The foam body of the present embodiment can also be used in applications other than a scaffold for cultured meat, for example, in foods other than cultured meat, chemical products, chemicals, and the like.

EXAMPLES

Hereinafter, the present invention will be described in more detail using Examples and Comparative Examples. The present invention is not limited to these examples.

Example 1

First, distilled water was added in a 150 mL disposable cup (a cylindrical type) and stirred with a homogenizer. The rotational speed of the homogenizer was set at about 8000 rpm. The amount of the distilled water added was adjusted so that the total weight of materials in the cup would be 100 parts by weight. Next, 1.5 parts by weight of a hydroxypropyl methylcellulose (HPMC: METHOCEL (registered trademark) E19 manufactured by Dow Inc.) powder and 0.1 parts by weight of a glucomannan (GM: RHEOLEX (registered trademark) LM manufactured by Shimizu Chemical Corporation) powder were added little by little in this order and dissolved in the water. A solution containing, as a foaming agent, HPMC and GM was obtained in this manner.

Subsequently, the solution obtained was stirred with the homogenizer, thereby foaming the solution and forming bubbles. Under continuous stirring with the homogenizer, 1.2 parts by weight of a sodium alginate (ALG: I-3G manufactured by KIMICA Corporation) powder was added in portions to the solution. When the appearance of the solution became stable, the rotation rate of the homogenizer was gradually increased. Eventually, the rotational speed of the homogenizer was set at 20000 rpm. Then, the rotational speed was decreased to 18000 to 19000 rpm to eliminate large bubbles formed during the stirring.

Next, a dispersion consisting of 0.24 parts by weight of calcium carbonate (manufactured by FUJIFILM Wako Pure Chemical Corporation: special grade) and water was produced using a 13.5 mL screw bottle. Specifically, first, half the required amount of the distilled water was mixed with the calcium carbonate in consideration of poor water solubility of calcium carbonate. The resulting mixture was subjected to sonication with an ultrasonic cleaner for about 15 minutes to disperse the calcium carbonate in the water. The dispersion was added to the solution in the disposable cup. Next, the rest of the distilled water was added to the screw bottle to wash the calcium carbonate off the inner wall of the screw bottle, and the mixture was added to the solution in the disposable cup. At that time, a food dye was added into the disposable cup so that the stirring condition can be visually seen.

After the dispersion containing the calcium carbonate was added to the solution in the disposable cup, the solution was stirred again using the homogenizer. The rotation rate of the homogenizer was 18000 rpm then.

Next, 0.432 parts by weight of a glucono-delta-lactone (GDL: Fuji-glucon (registered trademark) manufactured by FUSO CHEMICAL CO., LTD.) powder was slowly added to the solution. The homogenizer was turned off at the moment when the solution was uniformly colored with the food dye because the uniform coloring of the solution is considered as a sign of uniform mixing of the GDL in the solution. It should be added that gelation of the solution starts after the addition of the GDL to the solution. An excessive increase in solution temperature by stirring with the homogenizer accelerates the gelation rate, making it difficult to uniformly progress the gelation. After the addition of the GDL, the stirring was shortened and, additionally, the solution was cooled, as necessary, to prevent the solution temperature from excessively increasing. The solution was cooled by bringing the outer wall of the disposable cup into contact with iced water.

Next, the disposable cup was left to stand. A crosslinking reaction of a plurality of alginic acid molecules via a divalent calcium ion progressed in the solution, thereby forming a gel product. The duration (duration before the start of the gelation) from the addition of the GDL to loss of the flowability of the solution was 15 seconds.

Next, the gel product was taken out of the disposable cup. As shown in FIG. 1A, the gel product was in a cylindrical shape having a height of about 5 cm.

Figure 1B:
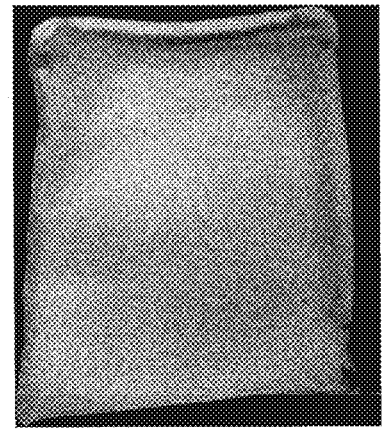
FIG. 1B shows the gel product cut into a sheet shape in Example 1.
Figure 2:
FIG. 2 is a scanning electron microscope (SEM) image showing a cross-section of the foam body of Example 1.
Figure 3:
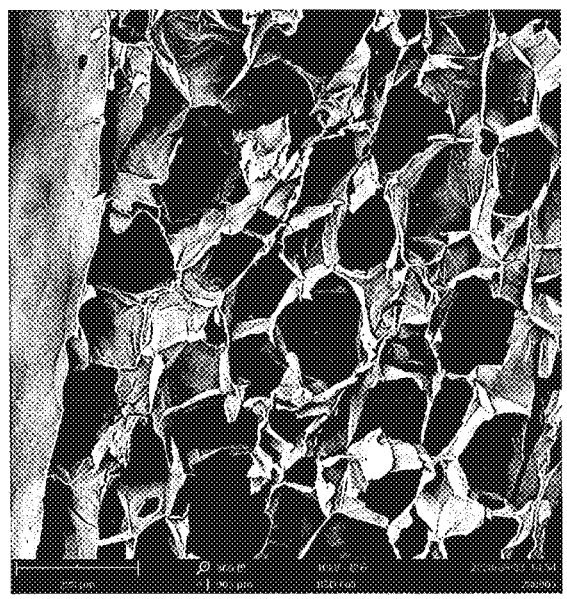
FIG. 3 is a SEM image showing a cross-section of a foam body of Example 2.
Figure 4:
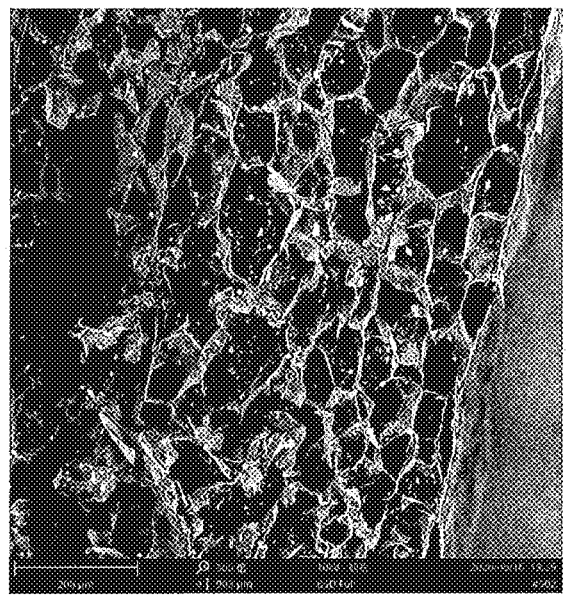
FIG. 4 is a SEM image showing a cross-section of a foam body of Example 4.
Figure 5:
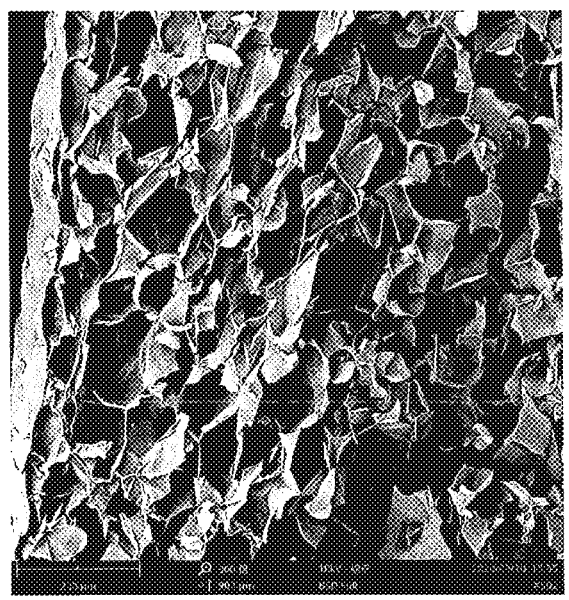
FIG. 5 is a SEM image showing a cross-section of a foam body of Example 8.
Figure 6:
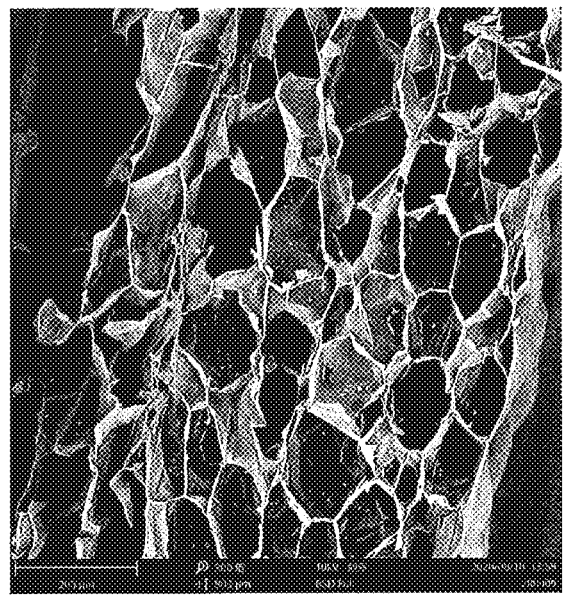
FIG. 6 is a SEM image showing a cross-section of a foam body of Example 9.
Figure 7:
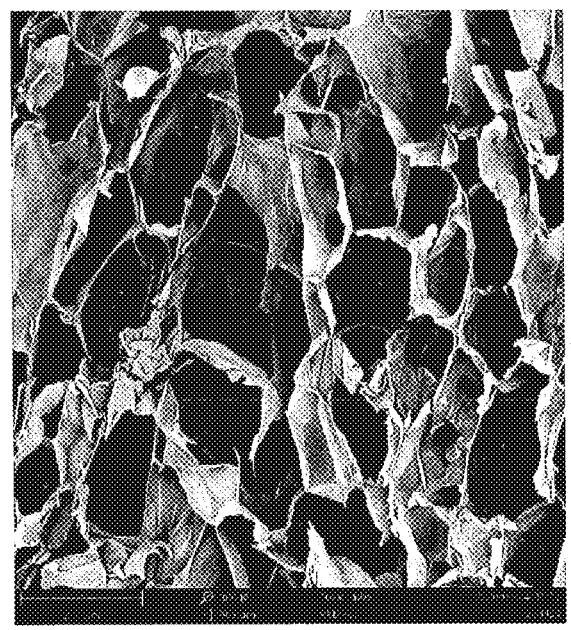
FIG. 7 is a SEM image showing a cross-section of a foam body of Example 10.
Figure 8:
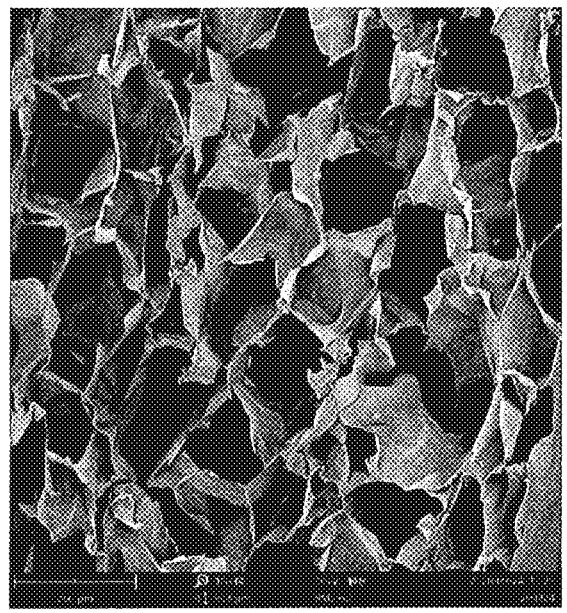
FIG. 8 is a SEM image showing a cross-section of a foam body of Example 11.
Figure 9:
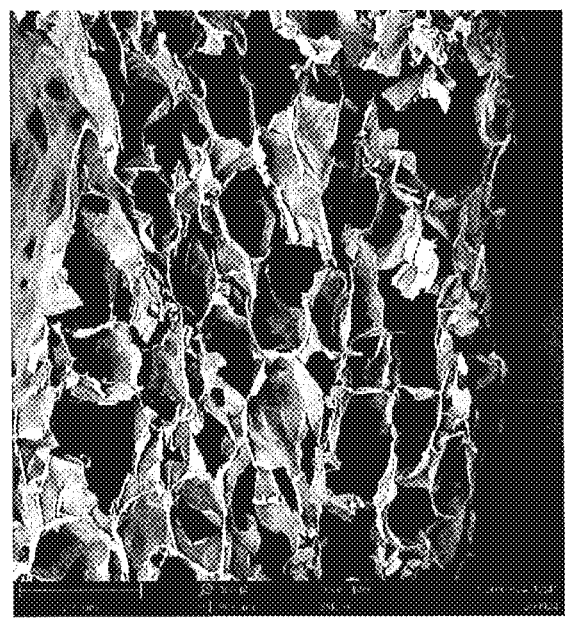
FIG. 9 is a SEM image showing a cross-section of a foam body of Example 12.
Figure 10:
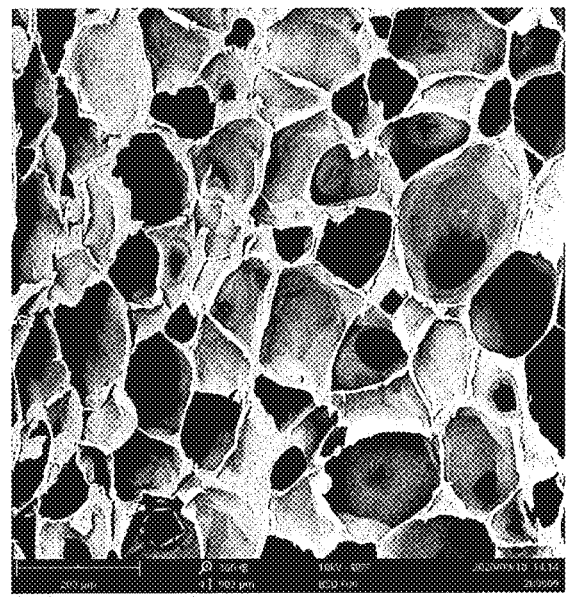
FIG. 10 is a SEM image showing a cross-section of a foam body of Comparative Example 1.
Figure 11:
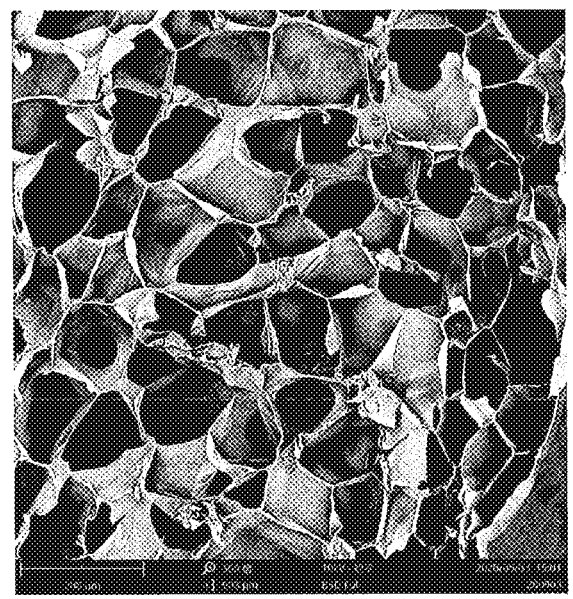
FIG. 11 is a SEM image showing a cross-section of a foam body of Comparative Example 2.
Figure 12:
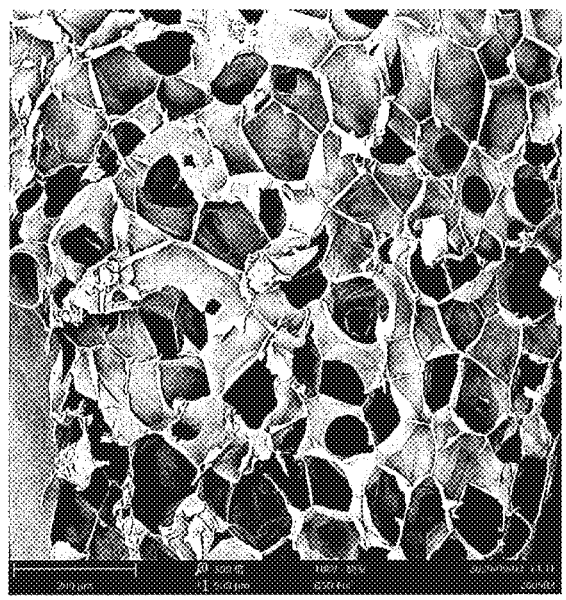
FIG. 12 is a SEM image showing a cross-section of a foam body of Comparative Example 3.
Figure 13:
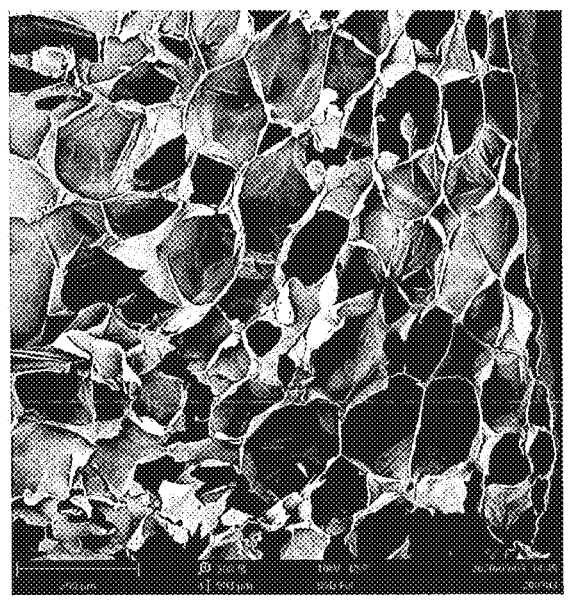
FIG. 13 is a SEM image showing a cross-section of a foam body of Comparative Example 4.

Next, cuts were made on a surface of the gel product at given intervals using a wire cutter. Next, the gel product was cut using a normal cutter. A sheet-shaped gel product, as shown in FIG. 1B, having a thickness of 7 mm was obtained in this manner.

Next, the sheet-shaped gel product was placed on an aluminum tray on which a sheet of parchment paper was laid, and was dried at 90° C. for 2 hours. A dried product was obtained in this manner. The thickness of the dried product was adjusted to 5 mm by slicing off a skin layer formed on a surface of the dried product with a cutter. A foam body of Example 1 was obtained in this manner.

Examples 2 to 12 and Comparative Examples 1 to 4

Foam bodies of Examples 2 to 12 and Comparative Examples 1 to 4 were produced in the same manner as in Example 1, except that the amounts of the materials added were changed as shown in Table 1. The production conditions in Comparative Example 1 were set by reference to the manufacturing conditions disclosed in Patent Literatures 2 and 3. In Comparative Example 1, glycerin and sorbitol were also added as plasticizers to the solution at the time of the addition of the sodium alginate to the solution. Additionally, the production conditions in Comparative Examples 2 to 4 were set to see the effect of the plasticizers under the manufacturing conditions disclosed in Patent Literatures 2 and 3. It should be noted that in Comparative Examples 1 to 4, the skin layer on a surface of the dried product was not sliced off, and the dried product was regarded as a foam body.

Next, the foam bodies of Examples and Comparative Examples were each evaluated as follows. Table 1 shows the evaluation results.

[Elastic Modulus M]

First, the foam body in the dry state was cut into a cube having a length of 10 mm, a width of 10 mm, and a thickness of 5 mm. This cubic foam body was immersed in 22±3° C. distilled water for 4 hours. The foam body was taken out of the water, and excess water on the surfaces of the foam body was removed. A specimen having a post-immersion thickness of 5±1 mm was obtained in this manner. Next, the specimen was set on a dynamic viscoelastic measurement apparatus (RSA-G2 manufactured by TA Instruments) for solids. The measurement apparatus has an upper jig ($\varphi 15$ mm) and a lower jig ($\varphi 25$ mm) as compression jigs. Stress and strain caused in the specimen were measured using the measurement apparatus by applying a load to the specimen for 5 seconds to compress the specimen in a thickness direction at 0.5 mm/sec. A stress caused in the specimen when the specimen was decompressed by 10% of the initial thickness was determined, and the elastic modulus M of the foam body was calculated from the determined value.

[Density]

First, the foam body in the dry state was cut into a given shape. The volume and wight of the foam body were measured, and the apparent density of the foam body was calculated from the volume and wight values. Then, the foam body was immersed in 22±3° C. water for 4 hours. The foam body was taken out of the water and excess water on the surfaces of the foam body was removed. A foam body in a wet state was obtained in this manner. The volume and wight of the foam body in a wet state were measured, and the apparent density of the foam body in a wet state was calculated from the volume and wight values.

[Porosity]

The porosity of the foam body was calculated from the true density of the foam body and the volume and weight measured to calculate the apparent density of the foam body. The true density of the foam body was calculated from the specific gravities of the components included in the foam body.

[Foaming Ratio]

A ratio of the true density of the foam body to the apparent density of the foam body in the dry state was calculated, and the obtained value was defined as the foaming ratio of the foam body.

[pH Test]

The above pH tests 1 and 2 were performed, and the pH of each water in which the foam body (specimen) was immersed was measured. For the pH test 2, the water in an amount of 50 mL in which the specimen had been immersed for 18 hours was also measured for its pH.

[Culture Test]

First, a 6 mm diameter disc was punched out from the foam body in the dry state and employed as a specimen. Next, sterilization treatment was performed in which the specimen was brought into contact with a 70 wt % aqueous solution of ethanol and left to stand for 30 minutes. Next, the specimen was washed with ultrapure water three times to remove ethanol from the specimen. The specimen was set in a 96-well plate. NIH 3T3 cells were added to the specimen in an amount of 20,000 cells/pcs and left to stand for about 30 minutes. Then, a culture medium was added around the specimen, and a culture test was performed at a $CO_2$ concentration of 5% and a temperature of 37° C. for 7 days. Propidium iodide (169-26281 manufactured by FUJIFILM Wako Pure Chemical Corporation) was added to the culture liquid to achieve a final concentration of 1 ug/mL, and then the cells were observed with a microscope. A cell colored throughout was determined as a dead cell. The specimen where dead cells accounted for less than 20% was defined as "culturable (○)" and the specimen where dead cells accounted for 20% or more was defined as "unculturable (x)".

[Calcium Carbonate Content]

First, the foam body in the dry state was crushed to produce a flaky measurement sample having a particle diameter of about several mm. An amount of 10 mL of a 0.1 mol/L aqueous HCl solution was added to 50 mg of the measurement sample, and sonication was performed for 60 minutes. This caused generation of calcium ion from all calcium carbonate included in the measurement sample.

Next, the measurement sample was filtered using a funnel. The measurement sample was washed then with 24 mL of distilled water. The concentration of calcium ion in the resulting filtrate was measured by subjecting the filtrate to ICP mass spectrometry. The calcium carbonate content in the foam body was calculated from the measurement result. The calcium ion used for the cross-linkage of the plurality of alginic acid molecules was not contained in the filtrate.

TABLE 1

| | | | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|---|---|
| Materials (parts by weight) | Sodium alginate | | 1.2 | 1.2 | 1.2 | 1.2 | 1.2 | 1.2 | 1.2 | 1.2 | 1.2 |
| | Foaming agent | HPMC | 1.5 | 1.5 | 1.5 | 1.5 | 1.5 | 1.5 | 1.5 | 1.5 | 1.5 |
| | | GM | 0.1 | 0.1 | 0.1 | 0.1 | 0.1 | 0.1 | 0.1 | 0.1 | 0.1 |
| | Acid generator | GDL | 0.432 | 0.648 | 0.864 | 1.08 | 1.296 | 1.728 | 2.16 | 1.296 | 0.324 |
| | Compound (C) | $CaCO_3$ | 0.24 | 0.36 | 0.48 | 0.6 | 0.72 | 0.96 | 1.2 | 0.36 | 0.36 |
| | Plasticizer | Glycerin | — | — | — | — | — | — | — | — | — |
| | | Sorbitol | — | — | — | — | — | — | — | — | — |
| | Total | | 3.472 | 3.808 | 4.144 | 4.48 | 4.816 | 5.128 | 6.16 | 4.456 | 3.484 |
| Weight ratio R1 ($CaCO_3$/ALG) | | | 0.20 | 0.30 | 0.40 | 0.50 | 0.60 | 0.80 | 1.0 | 0.30 | 0.30 |
| Weight ratio R2 (GDL/$CaCO_3$) | | | 1.80 | 1.80 | 1.80 | 1.80 | 1.80 | 1.80 | 1.80 | 3.60 | 0.90 |
| Duration before start of gelation (s) | | | 15 | 10 | — | 5 | — | — | — | 5 | 15 |
| Presence or absence of skin layer | | | Absence | Absence | Absence | Absence | Absence | Absence | Absence | Absence | Absence |
| Elastic modulus M (Pa) | | | 19601 | 14099 | 17118 | 43385 | 20650 | 55355 | 75471 | 32852 | 14914 |
| pH test 1 | pH of 1.5 mL water | | 9.72 | 9.22 | — | 8.61 | — | — | — | 5.13 | 9.95 |
| pH test 2 | pH of 50 mL water | | 8.93 | 8.85 | — | 8.88 | — | — | — | 8.46 | 9.08 |
| | pH of 1.5 mL water | | 7.3 | 8.37 | — | 9.58 | — | — | — | 7.96 | 8.68 |
| True density of foam body (g/cm³) | | | 1.41 | 1.43 | 1.44 | 1.45 | 1.46 | 1.47 | 1.49 | 1.41 | 1.44 |
| Apparent density of foam body (g/cm³) | | | 0.033 | 0.042 | — | 0.052 | — | — | — | 0.042 | 0.029 |
| Porosity (%) | | | 97.7 | 97.1 | — | 96.4 | — | — | — | 97.0 | 98.0 |
| Foaming ratio (times) | | | 43.0 | 34.3 | — | 28.0 | — | — | — | 33.3 | 49.8 |
| Density of foam body in wet state (g/cm³) | | | 1.471 | 0.856 | — | 0.689 | — | — | — | 0.479 | 1.315 |
| $CaCO_3$ content in foam body in dry state (%) | | | 7.42 | 10.87 | — | 12.81 | — | 14.85 | 16.27 | 6.70 | 8.39 |
| Culture test | | | ○ | ○ | ○ | ○ | ○ | — | — | ○ | ○ |

| | | | Ex. 10 | Ex. 11 | Ex. 12 | Comp. Ex. 1 | Comp. Ex. 2 | Comp. Ex. 3 | Comp. Ex. 4 |
|---|---|---|---|---|---|---|---|---|---|
| Materials (parts by weight) | Sodium alginate | | 1.5 | 1.2 | 1.5 | 2.22 | 2.22 | 2.22 | 1.2 |
| | Foaming agent | HPMC | 1.5 | 2.5 | 2.5 | 3.0 | 1.5 | 1.5 | 1.5 |
| | | GM | 0.1 | 0.1 | 0.1 | — | — | — | — |
| | Acid generator | GDL | 0.81 | 0.648 | 0.648 | 1.35 | 1.35 | 1.89 | 1 |
| | Compound (C) | $CaCO_3$ | 0.45 | 0.36 | 0.36 | 0.38 | 0.38 | 0.52 | 0.276 |
| | Plasticizer | Glycerin | — | — | — | 3 | — | — | — |
| | | Sorbitol | — | — | — | 9 | — | — | — |
| | Total | | 4.36 | 4.808 | 5.108 | 18.95 | 5.45 | 6.13 | 3.976 |
| Weight ratio R1 ($CaCO_3$/ALG) | | | 0.30 | 0.30 | 0.24 | 0.17 | 0.17 | 0.23 | 0.23 |
| Weight ratio R2 (GDL/$CaCO_3$) | | | 1.80 | 1.80 | 1.80 | 3.55 | 3.55 | 3.63 | 3.62 |
| Duration before start of gelation (s) | | | 10 | 10 | 13 | 3 | 3 | 1 | 10 |
| Presence or absence of skin layer | | | Absence | Absence | Absence | Presence | Presence | Presence | Presence |
| Elastic modulus M (Pa) | | | 40452 | 33306 | 18514 | 90969 | 89179 | 104691 | 116680 |
| pH test 1 | pH of 1.5 mL water | | 8.53 | 9.2 | 9.18 | 7.26 | 7.09 | 5.25 | 5.99 |
| pH test 2 | pH of 50 mL water | | 8.97 | 8.89 | 9.06 | 8.23 | 8.82 | 7.95 | 7.39 |
| | pH of 1.5 mL water | | 8.58 | 8.35 | 8.49 | 7.78 | 7.75 | 8.46 | 7.2 |
| True density of foam body (g/cm³) | | | 1.45 | 1.39 | 1.40 | 1.46 | 1.46 | 1.46 | 1.42 |
| Apparent density of foam body (g/cm³) | | | 0.052 | 0.037 | 0.040 | 0.143 | 0.070 | 0.053 | 0.053 |
| Porosity (%) | | | 96.4 | 97.3 | 97.1 | 90.2 | 95.2 | 96.4 | 96.3 |
| Foaming ratio (times) | | | 27.9 | 37.3 | 35.0 | 10.2 | 20.7 | 27.5 | 26.9 |
| Density of foam body in wet state (g/cm³) | | | 1.051 | 0.688 | 0.632 | 1.332 | 1.474 | 1.054 | 1.236 |
| $CaCO_3$ content in foam body in dry state (%) | | | — | — | — | — | — | — | — |
| Culture test | | | ○ | ○ | ○ | ○ | ○ | ○ | ○ |

As can be seen from Table 1, the elastic moduli M of the foam bodies of Examples 1 to 12 obtained under the manufacturing conditions of the present embodiment are $8 \times 10^4$ Pa or less, which is smaller than those of Comparative Examples 1 to 4. Incidentally, each of the foam bodies of Comparative Examples 1 to 4 has a skin layer on its surface; however, the higher elastic moduli M of Comparative Examples are not attributable to the skin layers, but to the whole foam bodies that are harder than those of Examples.

As can be understood from Examples and Comparative Examples, the duration before the start of the gelation is likely to be short under conditions where relatively large amounts of GDL and $CaCO_3$ are used. For example, in Example 4, the temperature of the solution greatly increased after the addition of GDL, and the solution was unable to be cooled sufficiently. Consequently, the duration before the start of the gelation was as short as 5 seconds, and gelation did not uniformly progress. Additionally, too much $CaCO_3$ was also confirmed from a later-described scanning electron microscope image of a cross-section of the foam body of Example 4. It is inferred that the foam body of Example 4 has a relatively large apparent density for these reasons.

Next, 5 mm thick fillets of salmon and tuna were prepared. Each fillet was set on a dynamic viscoelastic measurement apparatus for solids and measured for its elastic modulus M by the above-described method. According to the measurement results, salmon has an elastic modulus M of 4750 Pa while tuna has an elastic modulus M of 22448 Pa. The elastic moduli M of the foam bodies of Examples 1 to 12 are comparable to those of salmon and tuna, from which it is inferred that the textures of the foam bodies are similar to those of salmon and tuna. This leads to the conclusion that the foam bodies of Examples 1 to 12 are suitable for producing a cultured meat having a good texture.

[Observation of Cross-Section]

Cross-sections of the foam bodies of Examples 1, 2, 4, and 8 to 12 and Comparative Examples 1 to 4 were observed using a scanning electron microscope (SEM). FIGS. 2 to 13 show the results. FIGS. 2 to 13 lead to the conclusion that in the foam bodies of Examples, the distance between two neighboring pores is smaller, i.e., a pore wall is thinner, than in Comparative Examples. Additionally, from FIGS. 2 to 13 and the results shown in Table 1, it can be confirmed that the smaller the apparent density of the foam body is, the more likely the pore wall is to be thin.

[Permeation Test]

Figure 14A:
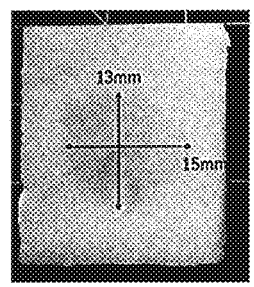
FIG. 14A shows a result of a permeation test for the foam body of Example 2 having no skin layer.

The foam body of Example 2 was subjected to the above-described permeation test and measured for the maximum diameter of an aqueous solution mark formed on a surface of the foam body. FIG. 14A shows the result. As can be seen from FIG. 14A, the maximum diameter of the aqueous solution mark was 15 mm.

Figure 14B:
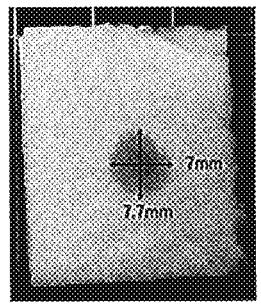
FIG. 14B shows the result of a permeation test for a dried product of Example 2 having a skin layer.

Moreover, the dried product (the skin layer on its surface had not been sliced off) obtained in Example 2 was subjected to the permeation test in the same manner. Specifically, the dried product was cut into a specimen having a length of 30 mm, a width of 30 mm, and a thickness of 2 mm such that the skin layer remained on one principal surface. The permeation test was performed for the specimen such that the aqueous solution was dropped onto the principal surface with the skin layer. FIG. 14B shows the result. As can be seen from FIG. 14B, the maximum diameter of the aqueous solution mark was 7.7 mm, which is smaller than that of the foam body of Example 2 having no skin layer. FIGS. 14A and 14B lead to the conclusion that a culture liquid is likely to permeate in the foam body having no skin layer and having pores opening at its surface.

INDUSTRIAL APPLICABILITY

The foam body of the present embodiment is suitable for a scaffold for producing cultured meat. The foam body of the present embodiment can also be used in applications other than a scaffold for cultured meat, for example, in foods other than cultured meat, chemical products, chemicals, and the like.

The invention claimed is:

1. A foam body comprising alginic acid and/or an alginate, and glucomannan wherein
    the foam body has an elastic modulus M, as determined by a test, of $8 \times 10^4$ Pa or less,
    in the test, the foam body is immersed in $22 \pm 3°$ C. water for 4 hours to prepare a specimen having a post-immersion thickness of $5 \pm 1$ mm, stress and strain caused in the specimen are measured by applying a load to the specimen for 5 seconds to compress the specimen in a thickness direction at 0.5 mm/sec, a stress caused in the specimen when the specimen is compressed by 10% of an initial thickness is determined, and a value obtained by dividing the stress by a corresponding strain is determined as the elastic modulus M.

2. The foam body according to claim 1 being edible.

3. The foam body according to claim 1, wherein the elastic modulus M is $1 \times 10^3$ Pa or more.

4. The foam body according to claim 1, wherein the foam body in a dry state has an apparent density of 0.05 g/cm$^3$ or less.

5. The foam body according to claim 1, comprising two or more additional polysaccharides other than the alginic acid and the alginate.

6. The foam body according to claim 1, comprising a cellulose derivative.

7. The foam body according to claim 1, comprising a cellulose derivative, wherein
    a weight ratio between the glucomannan and the cellulose derivative in the foam body is 0.1:99.9 to 9.9:90.1.

8. The foam body according to claim 1, comprising a compound that generates a divalent metal ion.

9. The foam body according to claim 8, wherein the compound is calcium carbonate.

10. The foam body according to claim 8, wherein a content of the compound in the foam body is 20 wt % or less.

11. The foam body according to claim 1, wherein the foam body in a dry state has a pore opening at a surface.

* * * * *